United States Patent [19]

Figala

[11] 4,272,507
[45] Jun. 9, 1981

[54] PHENYLAMINOTHIOPHENACETIC ACIDS, THEIR SYNTHESIS, COMPOSITIONS AND USE

[75] Inventor: Volker Figala, Allensbach, Fed. Rep. of Germany

[73] Assignee: Byk Gulden Lomberg Chemische Fabrik GmbH, Constance, Fed. Rep. of Germany

[21] Appl. No.: 41,313

[22] Filed: May 22, 1979

[30] Foreign Application Priority Data

May 24, 1978 [CH] Switzerland .................. 5687/78
Apr. 10, 1979 [CH] Switzerland .................. 3419/79

[51] Int. Cl.$^3$ .................. A61K 31/38; C07D 333/24
[52] U.S. Cl. .................. 424/275; 549/68
[58] Field of Search .................. 549/68; 424/275

[56] References Cited

U.S. PATENT DOCUMENTS 3,445,473  5/1969  Ruschig et al. .................. 549/68

*Primary Examiner*—Alan Siegel
*Attorney, Agent, or Firm*—Berman, Aisenberg & Platt

[57] ABSTRACT

Phenylaminothiophenacetic acids of formula I

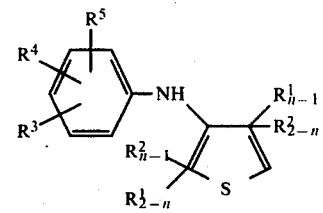

wherein
$R^1$ denotes a hydrogen atom, a chlorine atom, a bromine atom or a methyl group,
$R^2$ denotes a —CH$_2$—COOH group or a —CH$_2$—COOR$^6$ group,
$R^3$ denotes a hydrogen atom, a halogen atom, an alkyl group, an alkoxy group or a trifluoromethyl group,
$R^4$ has one of the meanings of $R^3$,
$R^5$ denotes a hydrogen atom, a halogen atom or an alkyl group,
$R^6$ denotes an alkyl group (with from 1 to 5 carbon atoms), which is optionally substituted by hydroxyl, hydroxyalkoxy or alkanoyloxy groups, or a benzyl group and
n denotes 1 or 2, and salts of the acids have outstanding antiphlogistic, analgesic and antipyretic activities.

13 Claims, No Drawings

PHENYLAMINOTHIOPHENACETIC ACIDS, THEIR SYNTHESIS, COMPOSITIONS AND USE

TECHNICAL FIELD

The invention relates to pharmacologically-active compounds and, more particularly, to phenylaminothiophenacetic acids, to processes for their preparation, to their use, to medicaments containing them and to intermediates in their synthesis. The compounds according to the invention are used in the pharmaceutical industry and for the preparation of medicaments.

BACKGROUND

3-Phenylaminothiophen-4-carboxylic acids, to which good antiphlogistic and antipyretic properties are attributed, are described in German Patent Specification No. 1,493,705. (*) The antiphlogistic action of the 2,3-dimethylphenyl compound proved comparable to that of phenylbutazone, and its antipyretic action proved to be superior. Further interesting representatives of this class of compound are the 2,6-dichlorophenyl derivative and the 2-methyl-3-chlorophenyl derivative [Alpermann, H. G., Arzneim.-Forsch. (Drug Res.), 20 (1970) 293 and 294] and the 2-chloro-3-methylphenyl derivative [Alpermann, H. G., et al., Arzneim.-Forsch. (Drug Res.), 22 (1972) 2146 and 2147], the actions of which are superior to those of phenylbutazone. Fibrinolytic properties are also attributed to various thiophencarboxylic acids [von Kaulla, K. N., Arzneim.-Forsch., 25, 152 to 155 (1975); von Kaulla, K. N., and Thilo, D., Klin. Wochensch., 48, 668 to 673 (1970); and Thilo, D., and von Kaulla, K. N., J. Med. Chem., 13, 503 to 510 (1970)].

(*) Corresponding to U.S. Pat. No. 3,445,473

STATEMENT OF THE INVENTION

Phenylaminothiophenacetic acids (=phenylaminothienylacetic acids) and their salts have outstanding pharmacological activity; the corresponding nitriles and esters are predominantly valuable intermediate products for the preparation of the pharmacologically-active phenylaminothiophenacetic acids and their salts.

Phenylaminothiophenacetic acids are, e.g., compounds of formula I wherein
$R^1$ denotes a hydrogen atom (—H), chloro, bromo or methyl;
$R^2$ denotes —CH$_2$—COOH or —CH$_2$—COOR$^6$;
$R^3$ denotes a hydrogen atom (—H), halo, alkyl, alkoxy or trifluoromethyl;
$R^4$ has one of the meanings of $R^3$;
$R^5$ denotes a hydrogen atom (—H), halo or alkyl;
$R^6$ denotes alkyl (with from 1 to 5 carbon atoms), which is optionally substituted by hydroxyl, hydroxyalkoxy or alkanoyloxy, or benzyl and
n denotes 1 or 2, and salts of the acids. These compounds are physiologically active and have significant antiphlogistic, analgesic and antipyretic properties.

They are prepared, e.g., by lyolysis of a corresponding functional carboxylic acid derivative of one of the formulae:

(IIa)　　(IIb)

(IIc)

(IId)

wherein
each of $R^1$ and $R^3$ to $R^5$ has its previously-ascribed meaning, and
G is a functional derivative of a carboxylic acid group. Such carboxylic acid derivatives are prepared by known methods from available starting materials.

Medicament compositions are conventionally compounded and prepared in standard dosage forms, particularly those suitable for oral administration. The active ingredient includes an effective amount of a pharmacologically-acceptable compound of Formula I. Such compositions are administered, e.g., orally to mammals afflicted with inflammation, pain, swelling and/or fever in effective doses at appropriate intervals and over a period sufficient to relieve, alleviate or eliminate the noted condition(s).

DEFINITION OF TERMS

Throughout the disclosure and claims a number of terms are repeatedly found. Whenever the following words and expressions appear in the text, they have the indicated meanings in the absence of a specific statement to the contrary.

analgesic—an agent that relieves pain; in this application particular emphasis is placed on relief of pain caused by inflammation.
alkanoyloxy—lower alkylcarbonyloxy, particularly those wherein the alkyl has from 1 to 3 carbon atoms, e.g. acetoxy and butyryloxy.
alkoxy—alkyloxy wherein the alkyl is as hereinafter defined and exemplified, preferably methoxy.
alkyl—straight-chain or branched saturated lower hydrocarbyl aliphatic ordinarily having from 1 to 5 carbon atoms, e.g. pentyl, butyl, propyl, ethyl, neopentyl, tert.-butyl, sec.-butyl, isopropyl and, preferably, methyl.
antiphlogistic—an agent counteracting inflammation.
antipyretic—an agent that reduces fever.
degree (°)—all degrees relate to temperature and are in degrees centigrade.

functional derivative—a carboxylic-acid-group derivative which is readily convertible by established procedures into a carboxylic acid group or a salt of such group; such derivatives constitute a well-defined and recognized genus which is known to organic synthesists; they include such radicals as a nitrilte (—CN); a carboxylic acid amide, e.g. —CO—NH$_2$; a carboxylic acid halide, e.g. —CO—Cl; a carboxylic acid lower-alkyl ester radical, e.g. —CO—O—CH$_3$ or —CO—O—C(CH$_3$)$_3$; and a carboxylic acid benzylester group.

halo—fluoro, bromo or, preferably, chloro.

hydroxyalkoxy—alkoxy (preferably having from 1 to 4 carbon atoms, such as methoxy, ethoxy and isobutoxy) substituted by from 1 to 3 hydroxyl groups, e.g. 2-hydroxyethoxy, 2,3-dihydroxypropoxy and 2-hydroxypropoxy.

lower—when applied to a radical having a straight or branched carbon chain, one wherein such chain has from 1 to 7 carbon atoms.

lyolyze—split by solvolysis, hydrogenolysis or thermolysis.

salt—since toxic salts are readily convertible into others which are non-toxic and are thus clearly useful, all salts are included in the subject invention; the pharmacologically-acceptable or biologically-tolerated salts (which constitute a well-established class) are preferred. Cations used for salt formation include those of alkali metals, e.g. lithium, sodium and potassium; alkaline-earth metals, e.g. magnesium and calcium; earth metals, e.g. aluminum; combinations of the preceding, e.g., in the form of basic magnesium aluminum complex salts; copper; cation acids or univalent or polyvalent organic nitrogen bases, particularly of organic amines, e.g. those of ethanolamine, diethanolamine, triethanolamine, ethylenediamine, dimethylamine, diethylamine, morpholine, piperazine, methylcyclohexylamine, glucosamine, N-methylglucamine, N-methylglucosamine, tert.-butylamine, dibutylamine, diisopropylamine, triethylamine, isopropylamine, 2-amino-2-thiazoline, quinoline and ammonia; and amino-acids, e.g. alanine, lysine, arginine and asparagine.

substituted alkyl—mono-, di- or (tri-hydroxy)alkoxyalkyl, e.g. 2-(2-hydroxyethoxy)ethyl and 2,3-dihydroxypropoxyethyl; hydroxyalkyl, e.g. 2-hydroxyethyl and 3-hydroxypropyl; or alkanoyloxyalkyl, e.g. acetoxymethyl.

unit dose—a physically-determined unit which contains an individual amount of the active constituent mixed with a pharmaceutical diluent for the constituent or together with a pharmaceutical excipient. The amount of active compound is chosen so that one or more units are usually required for an individual therapeutic administration. However, the unit is optionally divisible, for example in the case of tablets provided with breaking grooves, if only a fraction, such as a half or one-quarter, of the divisible unit is required for an individual therapeutic administration.

DETAILS

Compounds—A select group (IA) of phenylaminothiophenacetic acids are those of formula I wherein $R^1$ denotes a hydrogen atom (—H), chloro, bromo or methyl, $R^2$ denotes —CH$_2$—COOH or —CH$_2$—COOR$^6$, $R^3$ denotes a hydrogen atom (—H), chloro, methyl or trifluoromethyl, $R^4$ has one of the meanings of $R^3$, $R^5$ denotes a hydrogen atom (—H) or chloro, $R^6$ denotes benzyl or alkyl (with from 1 to 4 carbon atoms) which is optionally substituted by acetoxy or 2-hydroxyethoxy, and n denotes 1, and salts of the acids.

Preferred representatives (IA') of this select group are those in which $R^1$ denotes a hydrogen atom (—H) or chloro, $R^2$ denotes —CH$_2$—COOH or —CH$_2$—COOR$^6$, $R^3$ denotes chloro, methyl or trifluoromethyl, $R^4$ denotes chloro or methyl, $R^5$ denotes a hydrogen atom (—H) or chloro and $R^6$ denotes 2-(2-hydroxyethoxy)ethyl, and the pharmacologically-tolerated salts of the acids.

Particularly preferred representatives (IA'') of of this select group are those in which $R^1$ denotes a hydrogen atom (—H), $R^2$ denotes —CH$_2$—COOH, $R^3$ denotes chloro or methyl, $R^4$ denotes chloro and $R^5$ denotes a hydrogen atom (—H), and their pharmacologically-tolerated salts.

A further select group (IB) of phenylaminothiophenacetic acids are those of formula I wherein $R^1$ denotes a hydrogen atom (—H) or methyl, $R^2$ denotes —CH$_2$—COOH or —CH$_2$—COOR$^6$, $R^3$ denotes a hydrogen atom (—H), chloro, methyl or trifluoromethyl, $R^4$ has one of the meanings of $R^3$, $R^5$ denotes a hydrogen atom (—H) or chloro, $R^6$ denotes benzyl or alkyl (with from 1 to 4 carbon atoms) which is optionally substituted by acetoxy or 2-hydroxyethoxy, and n denotes 2, and salts of the acids.

Preferred representatives (IB') of this further select group are those in which $R^1$ denotes a hydrogen atom (—H), $R^2$ denotes —CH$_2$—COOH or —CH$_2$—COOR$^6$, $R^3$ denotes chloro, methyl or trifluoromethyl, $R^4$ denotes chloro or methyl, $R^5$ denotes a hydrogen atom (—H) or chloro and $R^6$ denotes 2-(2-hydroxyethoxy)ethyl, and the pharmacologically-tolerated salts of the acids.

Particularly preferred representatives (IB'') of this further select group are those in which $R^1$ denotes a hydrogen atom (—H), $R^2$ denotes —CH$_2$—COOH, $R^3$ denotes chloro or methyl, $R^4$ denotes chloro and $R^5$ denotes a hydrogen atom (—H), and their pharmacologically-tolerated salts.

Representatives (IA) are preferable to (IB).

Examples of representative compounds of the invention are: 4-(2,3-dimethylanilino)-3-thiophenacetic acid, 4-(2,3-dimethylanilino)-3-thiophenacetic acid benzyl ester, 4-(2-fluoro-6-trifluoromethylanilino)-3-thiophenacetic acid, 4-(2-chloro-6-methylanilino)-3-thiophenacetic acid, 4-(2-chloro-6-methylanilino)-3-thiophenacetic acid 2-(2-hydroxyethoxy)ethyl ester, 4-(2-chloro-6-methylanilino)-3-thiophenacetic acid benzyl ester, 4-(2,4,6-trimethylanilino)-3-thiophenacetic acid, 4-(2,4,6-trichloroanilino)-3-thiophenacetic acid, 4-(2,4,6-trimethylanilino)-3-thiophenacetic acid 3-acetoxypropyl ester, 4-(2-bromoanilino)-3-thiophenacetic acid, 4-(2-methyl-4-trifluoromethylanilino)-3-thiophenacetic acid, 4-(4-fluoroanilino)-3-thiophenacetic acid, 4-(2,3-dichloroanilino)-3-thiophenacetic acid, 4-(2,3-dichloroanilino)-3-thiophenacetic acid methyl ester, 4-(2,3-dichloroanilino)-3-thiophenacetic acid 2-(2-hydroxyethoxy)ethyl ester, 4-(2,3-dichloroanilino)-3-thiophenacetic acid benzyl ester, 4-(2-chloro-5-methylanilino)-3-thiophenacetic acid, 4-(2-chloro-5-methylanilino)-3-thiophenacetic acid 2-acetoxymethyl ester, 4-(2-chloro-3-methylanilino)-3-thiophenacetic acid 3-acetoxypropyl ester, 4-(2-chloro-3-methylanilino)-3-thiophenacetic acid benzyl ester, 4-(2,4-dichloro-3-methylanilino)-3-thiophenacetic acid, 4-(2,4-dichloro-3-methylanilino)-3-thiophenacetic acid n-propyl ester, 4-(2,4-dichloro-5-methylanilino)-3-thiophenacetic acid, 4-(2,4-dichloro-5-methylanilino)-3-thiophenacetic acid sec.-butyl ester, 3-(2,3-dimethylanilino)-2-thiophenacetic acid, 3-(2,3-dimethylanilino)-2-thiophenacetic acid 2-(2-hydroxyethoxy)ethyl ester, 3-(2,4,6-trimethylanilino)-2-thiophenacetic acid, 3-(2,4,6-trichloroanilino)-2-thiophenacetic acid 3-(2-chloroanilino)-2-thiophenacetic acid, 3-(2-chloroanilino)-2-thiophenacetic acid 3-acetoxypropyl ester, 3-(2-chloroanilino)-2-thiophenacetic acid benzyl ester, 3-(2,3-dichloroanilino)-2-thiophenacetic acid, 3-(2,3-dichloroanilino)-2-thiophenacetic acid 2-butyryloxyethyl ester, 3-(2,3-dichloroanilino)-2-thiophenacetic acid benzyl ester, 3-(3-methylanilino)-2-thiophenacetic acid, 3-(3-methylanilino)-2-thiophenacetic acid isopropyl ester, 3-(3-methylanilino)-2-thiophenacetic acid benzyl ester, 3-(2,4-dichloro-3-methylanilino)-2-thiophenacetic acid, 3-(2,4-dichloro-3-methylanilino)-2-thiophenacetic acid 2-(2-hydroxyethoxy)ethyl ester, 3-(2,4-dichloro-3-methylanilino)-2-thiophenacetic acid benzyl ester, 4-(2-methyl-4-trifluoromethylanilino)-3-thiophenacetic acid, 3-(2-methyl-4-trifluoromethylanilino)-2-thiophenacetic acid n-butyl ester, 3-(2-methyl-4-trifluoromethylanilino)-2-thiophenacetic acid 2-acetoxymethyl ester, 3-(2,4-dichloroanilino)-2-thiophenacetic acid benzyl ester, 3-(2,5-dichloroanilino)-2-thiophenacetic acid, 4-(2,5-dichloroanilino)-3-thiophenacetic acid benzyl ester, 4-(2,3-dimethylanilino)-5-chloro-3-thiophenacetic acid, 4-(2,3-dimethylanilino)-5-chloro-3-thiophenacetic acid 2-(2-hydroxyethoxy)ethyl ester, 4-(2-chloro-6-methylanilino)-5-chloro-3-thiophenacetic acid, 4-(2-bromoanilino)-5-chloro-3-thiophenacetic acid, 4-(2,3-dichloroanilino)-5-methyl-3-thiophenacetic acid, 4-(2,3-dichloroanilino)-5-methyl-3-thiophenacetic acid benzyl ester, 4-(2-chloro-5-methylanilino)-5-methyl-3-thiophenacetic acid, 4-(2,4-dichloro-3-methylanilino)-5-chloro-3-thiophenacetic acid, 4-methyl-3-(2,3-dimethylanilino)-2-thiophenacetic acid, 4-methyl-3-(2,3-dimethylanilino)-2-thiophenacetic acid 2-acetoxymethyl ester, 3-(2-chloroanilino)-4-methyl-2-thiophenacetic acid, 3-(2-chloroanilino)-4-methyl-2-thiophenacetic acid benzyl ester, 3-(2,3-dichloroanilino)-4-methyl-2-thiophenacetic acid, 5-chloro-4-(2-methyl-4-trifluoromethylanilino)-3-thiophenacetic acid, 4-(2,4,6-trichloroanilino)-5-methyl-3-thiophenacetic acid and 5-chloro-4-(2,4,6-trichloroanilino)-3-thiophenacetic acid and salts of the acids.

Preferred compounds are: 4-(2,6-dichloroanilino)-3-thiophenacetic acid, 4-(2-chloro-6-methylanilino)-3-thiophenacetic acid, 4-(2,6-dichloro-3-methylanilino)-3-thiophenacetic acid, 3-(2,6-dichloroanilino)-2-thiophenacetic acid, 4-(2-chloro-3-methylanilino)-3-thiophenacetic acid, 4-(3-chloro-2-methylanilino)-3-thiophenacetic acid, 4-(2,6-dimethylanilino)-3-thiophenacetic acid, 5-chloro-4-(2,6-dichloroanilino)-3-thiophenacetic acid and 3-(2-chloro-6-methylanilino)-2-thiophenacetic acid and salts thereof.

Utility—When administered in a therapeutically-active and pharmacologically-tolerated amount, the compounds according to the invention are thus suitable for the treatment of a number of mammalian illnesses in which one or more symptoms of inflammation, pain and fever occur. Examples of such illnesses include the most diverse inflammatory and degenerative illnesses of the rheumatic type and of other inflammatory illness processes, for example acute and chronic polyarthritis, osteoarthritis, psoriatic arthritis, ankylosing spondylitis, polyarthroses, spondyloses, articular rheumatism and rheumatic fever; rheumatism of soft tissues, for example sciatica; painful post-operative swellings and inflammations; pain and swellings after hydrarthoses, sprains and breaks; pain and inflammations in connection with dental surgery; attacks of pain of the most diverse origins, for example neuritides, headaches and spasms; and human and animal illnesses which result in the above symptoms and require the use of an antiinflammatory, analgesic and/or antipyretic medicament.

The invention thus further relates to a process for the treatment of mammals suffering from one or more symptoms of inflammation, pain or fever. The process is characterized by administering to the sick mammal a therapeutically-active and pharmacologically-tolerated amount of one or more compounds of formula I and/or a salt thereof. The invention also relates to the use of the compounds according to the invention in combating the previously-indicated illnesses. The invention likewise comprises the use of the compounds according to the invention for the preparation of medicaments which are employed for combating the noted illnesses.

Pharmaceutical Compositions—The invention further relates to medicaments which are characterized by their content of one or more of the subject active compounds. If appropriate, the new medicaments contain, in addition to one or more new active compounds, pharmaceutical excipient for such active compounds. The content of active compound in these medicaments is from 1 to 95, preferably from 10 to 85, percent by weight, relative to the weight of the finished medicament.

The medicaments are preferably those which are administered orally, but they also include those administered rectally or parenterally, e.g. subcutaneously, intramuscularly or intravenously, as solutions of salts, and those applied topically (percutaneously). The pharmaceutical formulation of the active compound is advantageously in the form of unit doses which are adjusted to the desired administration. A unit dose is optionally in the form of a tablet, a capsule, a suppository or a measured volume of a powder, of granules, of a solution, of an emulsion, of a suspension, of a gel or of a cream.

The pharmaceutical formulations according to the invention, when in the form of a unit dose for administration to humans, contain 0.5 to 500 (advantageously about 2.5 to 250 and, in particular, about 5 to 125) mg of the subject active compound.

The unit doses for administration to lighter or heavier mammals are correspondingly chosen; thus, for example, unit doses for administration to large animals, such as cattle or horses, contain from 50 to 5,000 (advantageously 100 to 3,000 and, in particular, 150 to 2,000) mg of the active compound. The pharmaceutical formulations are, e.g., administered therapeutically 1 to 4 times daily, for example after each meal and/or in the evening. The dose administered depends on the frequency of administration, the period of treatment, the nature and severity of the illness and the weight, age and state of health of the patient. In general, the daily dose for mammals is between 0.01 and 35 mg/kg of body weight, preferably below 10 mg/kg of body weight. An appropriate daily dose for administration to humans is between 0.5 and 5 mg/kg of body weight.

The pharmaceutical formulations as a rule consist of the active compounds according to the invention and nontoxic, pharmaceutically-acceptable medicinal excipients which are used as an admixture in solid, semi-solid or liquid form, or as a means of encasing, for example in the form of a capsule, a tablet coating, a sachet or some other container for the therapeutically-active constituent. An excipient can, for example, serve in a conventional manner as a promoter of the absorption of the medicament by the body, as a formulation auxiliary, as a sweetener, as a flavoring agent, as a dye-stuff or as a preservative.

Examples of forms which may be administered orally are tablets, dragees, hard and soft capsules, for example those made of gelatin, dispersible powders, granules, aqueous and oily suspensions, emulsions, solutions or syrups.

Tablets optionally contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets may in addition be provided with a coating, which can also achieve (in a conventional manner) delayed dissolution and resorption of the medicament in the gastrointestinal tract and hence, for example, better toleration or a long period of action. Gelatin capsules may contain the medicament mixed with a solid diluent, for example calcium carbonate or kaolin, or with an oily diluent, for example olive oil, groundnut oil or paraffin oil.

Aqueous suspensions may contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene-sorbitol-monooleate, polyoxyethylene-sorbitan-monooleate or lecithin; preservatives, for example methylhydroxybenzoate or propylhydroxybenzoate; flavoring agents; and sweeteners, for example sucrose, lactose, dextrose or invert sugar syrup.

Oily suspensions optionally contain, for example, groundnut oil, olive oil, sesame oil, coconut oil or paraffin oil, and thickeners, such as beeswax, hard paraffin or cetyl alcohol; as well as sweeteners, flavoring agents and antioxidants.

Water-dispersible powders and granules contain, e.g., the medicaments mixed with dispersing agents, wetting agents and suspending agents, for example those previously mentioned, as well as with sweeteners, flavoring agents and dyestuffs. Emulsions contain, for example, olive oil, groundnut oil or paraffin oil, in addition to emulsifying agents, such as gum acacia, gum tragacanth, phosphatides, sorbitan monooleate or polyoxyethylene-sorbitan-monooleate, and sweeteners and flavoring agents.

Suppositories, which are prepared with the aid of binders which melt at the rectal temperature, for example cacao butter or polyethylene glycols, are used for rectal administration of the medicaments.

Sterile injectable aqueous solutions, isotonic salt solutions or other solutions, which may contain dispersing agents or wetting agents and/or pharmacologically-tolerated diluents, for example propylene glycol or butylene glycol, are used for parenteral administration of the medicaments.

In addition to the new phenylaminothiophenacetic acids, their esters and salts, the pharmaceutical formulations contain, for example, one or more pharmacologically-active constituents from other groups of medicaments, for example corticosteroids which have an antiphlogistic action (for example prednisone, prednisolone, dexamethasone and derivatives thereof); analgesics, such as pyrazoline derivatives, propoxyphene, phenacetin, salicylic acid derivatives and the like; muscle relaxants, such as pyridazine derivatives, carbamates (for example phenprobamate) and the like; substances with an antiulcerogenic action; antacids (such as magnesium trisilicate and aluminum hydroxide); substances which stimulate local blood flow, such as nicotinic acid derivatives and dimethylsulfoxide; local anaesthetics (such as lidocaine) and vitamins (such as vitamin $B_1$ chloride hydrochloride, vitamin $B_6$ hydrochloride, vitamin $B_{12}$ cyano complex and thiamine disulfide).

Synthesis—A functional carboxylic acid derivative of formula II

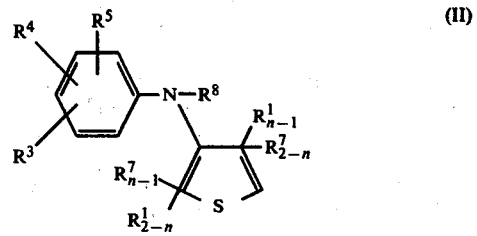

wherein $R^1$ denotes a hydrogen atom (—H), chloro, bromo or methyl, $R^3$ denotes a hydrogen atom (—H), halo, alkyl, alkoxy or trifluoromethyl, $R^4$ has one of the meanings of $R^3$, $R^5$ denotes a hydrogen atom (—H), halo or alkyl, $R^7$ denotes —$CH_2$—G or, together with $R^8$, —$CH_2$—CO—, $R^8$ denotes a hydrogen atom (—H) or, together with $R^7$, —CO—$CH_2$—, G denotes a functional derivative of a carboxylic acid group and n denotes 1 or 2, is lyolyzed (split by solvolysis, hydrogenolysis or thermolysis) to produce a compound of formula I or a salt thereof; the resulting acid or ester of formula I is then optionally conventionally converted into one another and/or into a salt.

An embodiment of the invention is a process for the preparation of phenylaminothiophenacetic acids IA and their salts which is characterized by lyolysis of functional phenylaminothiophenacetic acid derivatives (IIA) of formula II wherein $R^1$ denotes a hydrogen atom, a chlorine atom, a bromine atom or a methyl group,
$R^3$ denotes a hydrogen atom, a chlorine atom, a methyl group or a trifluoromethyl group,
$R^4$ has one of the meanings of $R^3$,
$R^5$ denotes a hydrogen atom or a chlorine atom,
$R^7$ denotes a —$CH_2$—G group or, together with $R^8$, a —$CH_2$—CO— group,
$R^8$ denotes a hydrogen atom or, together with $R^7$, a —CO—$CH_2$— group
G denotes a functional derivative of a carboxylic acid group and
n denotes 1,
to obtain compounds (IA), and optional halogenation of the resulting acids or esters of formula I and/or, in the customary manner, conversion into one another and/or into a salt.

In a preferred embodiment of the process, compounds (IIA) in which G represents a nitrile group, a carboxylic acid alkyl ester group (with from 1 to 7 carbon atoms in the alkyl radical), a carboxylic acid benzyl ester group or a carboxylic acid amide group are used as the starting materials.

A further embodiment of the invention is a process for the preparation of phenylaminothiophenacetic acids IB and their salts which is characterized by (a) lyolysis of functional phenylaminothiophenacetic acid derivatives (IIB) of formula II wherein
$R^1$ denotes a hydrogen atom (—H) or methyl,
$R^3$ denotes a hydrogen atom (—H), chloro, methyl or trifluoromethyl,
$R^4$ has one of the meanings of $R^3$,
$R^5$ denotes a hydrogen atom (—H) or chloro,
$R^7$ denotes —$CH_2$—G or, together with $R^8$, —$CH_2$—CO—,
$R^8$ denotes a hydrogen atom (—H) or, together with $R^7$, —CO—$CH_2$—,
G denotes a functional derivative of a carboxylic acid group and
n denotes 2,
to obtain compounds (IB), and optional conversion of the resulting acids or esters into one another and/or into salts in the customary manner, or (b) reduction of a phenylaminothiophenacetic acid derivative of formula III

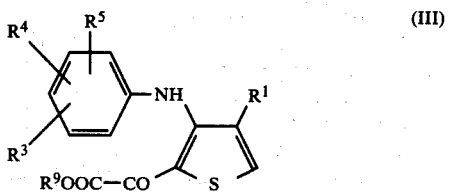

wherein
$R^1$ denotes a hydrogen atom (—H) or methyl,
$R^3$ denotes a hydrogen atom (—H), chloro, methyl or trifluoromethyl,
$R^4$ has one of the meanings of $R^3$,
$R^5$ denotes a hydrogen atom (—H) or chloro,
$R^9$ denotes a hydrogen atom (—H) or alkyl with from 1 to 5 carbon atoms, or a salt thereof and then optional conversion of the resulting acids or esters (IB) into one another and/or into salts in the customary manner.

In a preferred embodiment of process (a), compounds (IIB), in which $R^7$ represents —$CH_2$—G, $R^8$ represents a hydrogen atom (—H) and G represents a nitrile group, a carboxylic acid alkyl ester group with from 1 to 7 carbon atoms in the alkyl radical, a carboxylic acid benzyl ester group or a carboxylic acid amide group, are used as starting substances. Process (b) is preferred over variant (a).

Lyolysis of carboxylic acid derivatives encompasses solvolytic, hydrogenolytic or thermolytic splitting. Solvolytic splitting is, above all, hydrolysis and alcoholysis. A water-supplying medium, which consists completely or partly of water or of agents which split off water or $OH^-$ ions under the reaction conditions, is used for hydrolytic splitting of functional carboxylic acid derivatives of formula II. The reaction is carried out, e.g., as a homogeneous reaction, in which case it is usually carried out in the presence of a polar organic solvent or a solubilizing agent. Examples of solvents which are advantageously used are low-molecular alcohols, dioxan, acetone, low-molecular carboxylic acids, N-methylpyrrolidone, sulfolane or dimethylsulfoxide. However, the reaction is optionally effected as a heterogeneous reaction. The pH of the water-supplying medium depends on the chemical nature of the phenylaminothiophenacetic acid derivative employed and also on the nature of the desired compound of formula I; it can thus be neutral, acid or basic. It is adjusted to the desired value with acid, base or buffer. The reaction temperature is between 0° C. and the boiling point of the water-supplying medium, in general between 0° and 150° C. and in particular between 20° and 120° C. It also depends specifically on whether the reaction is carried out under pressure or under atmospheric pressure. The reaction time is between 10 minutes and 20 hours, depending on the mixture, the reaction temperature and other reaction parameters. When the hydrolytic splitting has ended, the produced phenylaminothiophenacetic acid is isolated by customary methods, for example by recrystallization or by acidification of its solution, if appropriate with concentration of its solution. For its purification, an alkaline solution thereof is, e.g., extracted with an organic solvent which is immiscible with the alkaline solution, for example diethyl ether, benzene, chlorobenzene, chloroform or methylene chloride.

Alcoholysis is preferably employed when the carboxylic acid derivative of formula II is one in which G represents a nitrile group. A medium which consists completely or partly of the alcohol concerned and a proton donor, for example methanol saturated with hydrochloric acid gas, is used for the alcoholysis. The reaction temperatures are between −20° and 50° C., in particular between 0° and 20° C. The reaction times are between 30 minutes and 10 hours (depending on the reaction temperature and other parameters). When the alcoholysis has ended, the formed esters are isolated by customary methods.

Lyolysis in the form of hydrogenolysis is carried out when the carboxylic acid derivative of formula II is one in which G represents a carboxylic acid benzyl ester group. It is effected under customary conditions, for example with hydrogen on palladium-on-charcoal or platinum, at a temperature of from −10° to 50° C., preferably at room temperature, under a pressure of from 1 to 200, preferably from 1 to 10, bars and in an inert solvent, such as methanol or acetic acid ethyl ester, or, preferably, in the presence of glacial acetic acid.

Lyolysis in the form of thermolysis is carried out when the phenylaminothiophenacetic acid derivative of formula II is one in which G represents a carboxylic acid tert.-alkyl ester group, preferably a tert.-butyl ester group.

This reaction is effected under conventional conditions, if appropriate in an inert organic solvent, for example chlorobenzene, xylene or toluene, without or preferably in the presence of an acid catalyst, such as p-toluenesulfonic acid, by heating to a temperature within the range of from 30° to 200° C., preferably from 70° to 150° C.

The phenylaminothiophenacetic acids of formula I are converted into their salts by direct alkaline solvolysis with hydroxyl ions from the phenylaminothiophenacetic acid derivatives of formula II. The employed alkaline reaction partner is appropriately that inorganic or organic base, the salt of which is desired. However, the salts are also obtained by reacting phenylaminothiophenacetic acids of formula I with the stoichiometric equivalent of a corresponding base, or by converting readily-soluble salts into sparingly-soluble salts by double decomposition or by converting any desired salt into a pharmacologically-tolerated salt.

Intermediates—The phenylaminothiophenacetic acid derivatives of formulae II, IIa, IIb, IIc and IId (employed as starting materials or intermediate products) are new compounds. They are prepared by known methods from available starting materials. Thus nitriles of formulae II, IIa and IIb are obtained from the corresponding halomethyl compounds, i.e. from compounds of formulae II, IIa or IIb in which G is halo, preferably bromo or chloro, by reaction with alkali-metal cyanides or alkaline-earth-metal cyanides, such as sodium cyanide, potassium cyanide or barium cyanide. The reaction is appropriately carried out in an aprotic dipolar solvent, for example dimethylformamide, or in a two-phase system in the presence of a phase transfer catalyst, such as benzyltrimethylammonium chloride, at temperatures of from 0° to 80° C.

Phenylaminothiophenacetic acid esters of formula II, IIa and IIb are readily accessible from the nitriles by alcoholysis. They are also accessible from the free acids of formula I by reaction with alcohols under conditions which split off water or by reaction of acids and salts with alkylating agents; for example benzyl esters are obtained by reacting silver salts with benzyl halides.

Halomethyl compounds are obtained by reducing corresponding phenylaminothiophen-carboxylic acids or carboxylic acid esters and subsequently halogenating the products. Examples of suitable reducing agents are sodium boranate, sodium/ethanol or lithium aluminum hydride. The reaction is preferably carried out in an inert solvent, such as an open-chain or cyclic ether, for example diethyl ether or tetrahydrofuran, at temperatures between 0° and 25° C. The resulting hydroxymethyl compounds are converted into the halomethyl compounds by reaction with a hydrogen halide, such as hydrogen chloride or hydrogen bromide. The reaction is effected in a polar, preferably aqueous medium, for example in concentrated hydrochloric acid, at a temperature within the range of from 10° to 50° C.

4-Phenylaminothiophen-3-carboxylic acids are obtained according to German Patent Specification No. 1,493,705. The corresponding esters are obtained by reaction of these acids with alcohols in a manner which is known per se. 3-Phenylaminothiophen-2-carboxylic acids or their esters are obtained by a process analogous to that of German Patent Specification No. 1,493,705 by reaction of 3-oxo-tetrahydrothiophen-2-carboxylic acid methyl ester or ethyl ester [Moore, E. E., and Moore, M. B., *J. Am. Chem. Soc.*, 68 (1946) 910; Erastov, O. A., and Ignat'eva, S. N., *Khim. Geterotsikl. Soedin.*, 1971, 7(11)1473 to 1480] with anilines substituted by $R^3$, $R^4$ and $R^5$, and subsequent dehydrogenation and, if appropriate, hydrolysis.

The subsequent halogenation of resulting compounds (IA), which is optionally carried out, is effected by processes which are known per se. Examples of possible halogenating agents for the halogenation of the thiophen ring are the free halogens, chlorine and bromine, N-halo-amides and -imides, sulfuryl chloride or phosphorus pentachloride. The reaction with the halogenating agent can be carried out in known manner, for example in an inert, non-aqueous solvent, such as a chlorinated hydrocarbon or glacial acetic acid (for example using chlorine, bromine or sulfuryl chloride), at temperatures of from −40° C. to 20° C., preferably at from −20° to 0° C., using excess or preferably equivalent amounts of the halogenating agent. As a rule, the reaction is complete within a period of from 10 minutes to 2 hours after the addition of the halogenating agent.

The hydrolysis of phenylaminothiophenacetic acid lactams of formulae II, IIc or IId [i.e. compounds of formula II in which $R^7$, together with $R^8$, denote a $-CH_2-CO-$ group and $R^8$, together with $R^7$, denote a $-CO-CH_2-$ group] is effected in a manner which is known per se by alkaline or acid saponification in a polar solvent, such as an alcohol, for example methanol, at temperatures of from 20° C. up to the boiling point of the solvent.

In general, the reaction is completed within about 2 hours, depending on the reaction temperature.

The reduction of the phenylaminothiophenacetic acid derivatives of formula III is effected, in a manner which is known per se, by reaction with a suitable reducing agent, for example sodium borohydride, in an inert solvent, such as tetrahydrofuran or dimethylformamide, at a temperature of from 0° up to the boiling point of the solvent, preferably at from 50° to 80° C. The reaction time is from 1 to 5 hours, depending on the temperature.

Compounds of formula III are obtained by reacting corresponding 3-phenylaminothiophens with oxalic acid alkyl ester chlorides and, if appropriate, subsequently saponifying the products.

The reaction is effected in the presence of an auxiliary base, such as pyridine or triethylamine, in an inert solvent, such as a cyclic or open-chain ether, for example tetrahydrofuran or diethyl ether, at temperatures between 0° and 50° C., preferably at room temperature.

3-Phenylaminothiophens are obtained by decarboxylation of 4-phenylamino-3-thiophencarboxylic acids, for example, by heating to a temperature within the range of from 120° to 200° C.

The hydroxymethyl compounds and halomethyl compounds are relatively unstable compounds as crude products; they are thus appropriately further reacted immediately after being obtained, purification operations being dispensed with if possible.

EXAMPLES

The examples which follow illustrate the invention in more detail. The abbreviations m., bp. and d. denote melting point, boiling point and decomposition point, respectively. All temperatures are in degrees centigrade (°C.).

EXAMPLE 1

31 g (0.11 mole) of 4-(2,6-dichloroanilino)-3-thiophenacetonitrile are boiled in a solution of 110 g of sodium hydroxide in 450 ml of water and 220 ml of methanol for 4 hours. The mixture is diluted with 2 liters of warm water and extracted with toluene, the aqueous phase is acidified and the precipitate of 4-(2,6-dichloroanilino)-3-thiophenacetic acid, which has formed, is filtered off. The precipitate is boiled up with diisopropyl ether and dried; it then melts at 179° to 180°.

4-(2-Chloroanilino)-3-thiophenacetic acid (m. 125° to 126.5°), 4-(2,6-dimethylanilino)-3-thiophenacetic acid (m. 152.5° to 153°), 4-(2-chloro-6-methylanilino)-3-thiophenacetic acid (m. 168° to 169°), 4-(4-methoxy-2-methylanilino)-3-thiophenacetic acid, 4-(2-chloro-3-methylanilino)-3-thiophenacetic acid (m. 105° to 106°) and 4-(3-trifluoromethylanilino)-3-thiophenacetic acid (m. 108° to 109°) are obtained analogously from: 4-(2-chloroanilino)-3-thiophenacetonitrile, 4-(2,6-dimethylanilino)-3-thiophenacetonitrile, 4-(2-chloro-6-methylanilino)-3-thiophenacetonitrile, 4-(4-methoxy-2-methylanilino)-3-thiophenacetonitrile, 4-(2-chloro-3-methylanilino)-3-thiophenacetonitrile and 4-(3-trifluoromethylanilino)-3-thiophenacetonitrile, respectively, by boiling with methanolic sodium hydroxide solution and appropriate working up of the mixture.

EXAMPLE 2

26.3 g (0.1 mole) of 4-(3-chloro-2-methylanilino)-3-thiophenacetonitrile are introduced into 135 ml of concentrated sulfuric acid; the resulting mixture is stirred at 20° for 1 hour; 49 ml of water are then added dropwise and the obtained mixture is heated to 100° for 3 hours. It is poured onto ice, and the precipitate, which has formed, is filtered off. Recrystallization from diisopropyl ether gives 4-(3-chloro-2-methylanilino)-3-thiophenacetic acid. m. 126° to 128°.

4-(2,6-Dichloro-3-methylanilino)-3-thiophenacetic acid (m. 159° to 160°), 4-(2-chloro-3-methylanilino)-3-thiophenacetic acid (m. 105° to 106°), 4-(2,6-difluoroanilino)-3-thiophenacetic acid (m. 151°), 4-(2,6-dimethylanilino)-3-thiophenacetic acid (m. 152.5° to 153°), 5-chloro-4-(2,6-dichloroanilino)-3-thiophenacetic acid (d. 141° to 142°), 4(2-chloroanilino)-5-methyl-3-thiophenacetic acid (m. 196°) and 4-(2,6-dichloroanilino)-5-methyl-3-thiophenacetic acid (m. 155° to 156°) are obtained analogously from: 4-(2,6-dichloro-3-methylanilino)-3-thiophenacetonitrile, 4-(2-chloro-3-methylanilino)-3-thiophenacetonitrile, 4-(2,6-difluoroanilino)-3-thiophenacetonitrile, 4-(2,6-dimethylanilino)-3-thiophenacetonitrile, 5-chloro-4-(2,6-dichloroanilino)-3-thiophenacetonitrile, 4-(2-chloroanilino)-5-methyl-3-thiophenacetonitrile and 4-(2,6-dichloroanilino)-5-methyl-3-thiophenacetonitrile, respectively, by saponification with concentrated sulfuric acid.

EXAMPLE 3

31 g (0.11 mole) of 4-(2,6-dichloroanilino)-3-thiophenacetonitrile are dissolved in 30 ml of methanol. The solution is saturated with hydrogen chloride gas at 10° and left to stand at 10° for four hours. It is then poured onto 200 ml of water, extracted with 100 ml of diethyl ether; the ethereal phase is washed with 50 ml of water, dried and concentrated. 4-(2,6-Dichloroanilino)-3-thiophenacetic acid methyl ester is obtained as an oil.

4-(2,6-dichloroanilino)-3-thiophenacetic acid ethyl ester (m. 64°–65° C.) is obtained analogously by dissolving the acetonitril in ethanol instead of methanol.

4-(2-Chloro-6-methylanilino)-3-thiophenacetic acid methyl ester (m. 90° to 100°) is obtained analogously from 4-(2-chloro-6-methylanilino)-3-thiophenacetonitrile by leaving this compound to stand in methanolic hydrochloric acid.

EXAMPLE 4

(a) The nitriles listed in Examples 1 to 3 are obtained in the following way:

29.2 g (0.1 mole) of 3-(2,6-dichloroanilino)-4-chloromethylthiophen and 13 g (0.2 mole) of potassium cyanide are dissolved in 250 ml of dimethylformamide and 0.5 ml of water, and the solution is warmed to 45° for one hour. It is poured onto ice and extracted with acetic acid ethyl ester, and the ethyl acetate phase is washed with water, dried over sodium sulfate and concentrated. 4-(2,6-Dichloroanilino)-3-thiophenacetonitrile remains as an oily residue and crystallizes out when left to stand (m. 81° to 83° C.).

4-(2-Chloroanilino)-3-thiophenacetonitrile (oil), 4-(2-chloro-6-methylanilino)-3-thiophenacetonitrile (oil), 4-(2-chloro-3-methylanilino)-3-thiophenacetonitrile, 4-(2,6-dichloro-3-methylanilino)-3-thiophenacetonitrile (oil), 4-(3-chloro-2-methylanilino)-3-thiophenacetonitrile (oil), 4-(2,6-difluoroanilino)-3-thiophenacetonitrile (oil), 4-(2-chloroanilino)-5-methyl-3-thiophenacetonitrile (oil) and 4-(2,6-dichloroanilino)-5-methyl-3-thiophenacetonitrile (m. 115° C.) are obtained analogously by reacting 3-(2-chloroanilino)-4-chloromethylthiophen, 3-chloromethyl-4-(2-chloro-6-methylanilino)thiophen, 3-chloromethyl-4-(2-chloro-3-methylanilino)thiophen, 3-chloromethyl-4-(2,6-dichloro-3-methylanilino)thiophen, 3-chloromethyl-4-(3-chloro-2-methylanilino)thiophen, 3-chloromethyl-4-(2,6-difluoroanilino)thiophen, 3-(2-chloroanilino)-4-chloromethyl-2-methylthiophen and 4-chloromethyl-3-(2,6-dichloroanilino)-2-methylthiophen, respectively, with potassium cyanide and appropriately working up the mixture.

Alternatively, the starting nitriles are obtained in the following manner:

2.72 g (10 mmoles) of 3-chloromethyl-4-(2-chloro-3-methylanilino)thiophen in 15 ml of dimethylsulfoxide are added dropwise to a solution of 650 mg of sodium cyanide in 15 ml of dimethylsulfoxide at 40°. The mixture is stirred for a further three hours, poured onto water and extracted three times with ethyl acetate. The combined extracts are washed with 50 ml each of 6 N hydrochloric acid and water, dried and concentrated. Crude 4-(2-chloro-3-methylanilino)-3-thiophenacetonitrile is obtained as an oil.

4-(2,6-Dimethylanilino)-3-thiophenacetonitrile, 4-(4-methoxy-2-methylanilino)-3-thiophenacetonitrile and 4-(3-trifluoromethylanilino)-3-thiophenacetonitrile are obtained analogously by reacting 3-chloromethyl-4-(2,6-dimethylanilino)thiophen, 3-chloromethyl-4-(4-methoxy-2-methylanilino)thiophen and 3-chloromethyl-4-(3-trifluoromethylanilino)thiophen, respectively, with sodium cyanide.

(b) The chloromethyl compounds are obtained in the following way:

27.4 g (0.1 mole) of 4-(2,6-dichloroanilino)-3-thiophenmethanol are dissolved in 800 ml of concentrated aqueous hydrochloric acid, and the solution is left to stand for eight hours, poured onto ice and extracted with toluene. The organic phase is washed with sodium bicarbonate solution, dried and concentrated. Recrystallization of the residue from petroleum ether gives 3-(2,6-dichloroanilino)-4-chloromethylthiophen (m. 89° to 92°).

3-(2-Chloroanilino)-4-chloromethylthiophen, 3-chloromethyl-4-(2,6-dimethylanilino)thiophen (m. 149°), 3-chloromethyl-4-(2-chloro-6-methylanilino)thiophen, 3-chloromethyl-4-(4-methoxy-2-methylanilino)thiophen, 3-chloromethyl-4-(2-chloro-3-methylanilino)thiophen (m. 60° to 63° C.), 3-chloromethyl-4-(3-trifluoromethylanilino)thiophen, 3-chloromethyl-4-(2,6-dichloro-3-methylanilino)thiophen (m. 68° to 70°), 3-chloromethyl-4-(3-chloro-2-methylanilino)thiophen, 3-chloromethyl-4-(2,6-difluoroanilino)thiophen, 3-(2-chloroanilino)-4-chloromethyl-2-methylthiophen (oil) and 4-chloromethyl-3-(2,6-dichloroanilino)-2-methylthiophen (m. 63° to 65°) are obtained analogously by reacting 4-(2-chloroanilino)-3-thiophenmethanol, 4-(2,6-dimethylanilino)-3-thiophenmethanol, 4-(2-chloro-6-methylanilino)-3-thiophenmethanol, 4-(4-methoxy-2-methylanilino)-3-thiophenmethanol, 4-(2-chloro-3-methylanilino)-3-thiophenmethanol, 4-(3-trifluoromethylanilino)-3-thiophenmethanol, 4-(2,6-dichloro-3-methylanilino)-3-thiophenmethanol, 4-(3-chloro-2-methylanilino)-3-thiophenmethanol, 4-(2,6-difluoroanilino)-3-thiophenmethanol, 4-(2-chloroanilino)-5-methyl-3-thiophenmethanol and 4-(2,6-dichloroanilino)-5-methyl-3-thiophenmethanol, respectively, with aqueous hydrochloric acid.

(c) The methanols are prepared in the following manner:

57.63 g (0.2 mole) of 4-(2,6-dichloroanilino)-3-thiophencarboxylic acid (dissolved in 350 ml of tetrahydrofuran) are added dropwise to a suspension of 7.59 g (0.2 mole) of lithium aluminum hydride in 170 ml of absolute tetrahydrofuran at 15° in the course of one hour, while stirring and under nitrogen. Stirring is then continued at room temperature for one hour. The reaction mixture is hydrolyzed with 2 liters of ice-cold water, acidified to pH 5 with dilute sulfuric acid and extracted with 1.5 liters of ethyl acetate. The extract is washed with 100 ml of 2 N sodium bicarbonate solution, dried over sodium sulfate and concentrated, 4-(2,6-dichloroanilino)-3-thiophenmethanol being obtained in almost quantitative yield as a viscous oil which slowly solidifies. Recrystallization from cyclohexane gives pure 4-(2,6-dichloroanilino)-3-thiophenmethanol (m. 96° to 97°).

4-(2-Chloroanilino)-3-thiophenmethanol (oil), 4-(2,6-dimethylanilino)-3-thiophenmethanol (m. 87°), 4-(2-chloro-6-methylanilino)-3-thiophenmethanol (m. 93° to 95°), 4-(4-methoxy-2-methylanilino)-3-thiophenmethanol, 4-(2-chloro-3-methylanilino)-3-thiophenmethanol and 4-(3-trifluoromethylanilino)-3-thiophenmethanol are obtained analogously by reducing 4-(2-chloroanilino)-3-thiophencarboxylic acid, 4-(2,6-dimethylanilino)-3-thiophencarboxylic acid, 4-(2-chloro-6-methylanilino)-3-thiophencarboxylic acid, 4-(4-methoxy-2-methylanilino)-3-thiophencarboxylic acid, 4-(2-chloro-3-methylanilino)-3-thiophencarboxylic acid and 4-(3-trifluoromethylanilino)-3-thiophencarboxylic acid, respectively, with lithium aluminum hydride.

4-(2,6-Dichloro-3-methylanilino)-3-thiophenmethanol (m. 121° to 122°), 4-(3-chloro-2-methylanilino)-3-thiophenmethanol (oil), 4-(2,6-difluoroanilino)-3-thiophenmethanol (m. 124° to 126°), 4-(2-chloroanilino)-5-methyl-3-thiophenmethanol (oil) and 4-(2,6-dichloroanilino)-5-methyl-3-thiophenmethanol (m. 64° to 65°) are obtained analogously by reducing 4-(2,6-dichloro-3-methylanilino)-3-thiophen-carboxylic acid methyl ester, 4-(3-chloro-2-methylanilino)-3-thiophen carboxylic acid methyl ester, 4-(2,6-difluoroanilino)-3-thiophencarboxylic acid methyl ester, 4-(2-chloroanilino)-5-methyl-3-thiophencarboxylic acid methyl ester and 4-(2,6-dichloroanilino)-5-methyl-3-thiophencarboxylic acid methyl ester, respectively, with lithium aluminum hydride.

(d) The anilinothiophencarboxylic acids and anilinothiophencarboxylic acid esters are obtained in the following way:

15.9 g (0.1 mole) of 4-oxotetrahydro-3-thiophencarboxylic acid methyl ester, 17.5 g of 2,6-dichloroaniline and 200 mg of p-toluenesulfonic acid are heated in 500 ml of dichloroethane for six hours using a water separator. The solution is cooled to $-25°$ and 52.5 g of bromine in 100 ml of dichloroethane are added dropwise. The mixture is stirred for a further 5 minutes; 100 ml of 10 percent strength (aq) sodium sulfite solution are added thereto, and the organic phase is separated off, washed with water and a sodium carbonate solution, dried and concentrated. Pure 4-(2,6-dichloroanilino)-3-thiophencarboxylic acid methyl ester is obtained after a bulb tube distillation (bp. $140°/10^{-2}$ Pascal).

4-(2,6-Dichloro-3-methylanilino)-3-thiophencarboxylic acid methyl ester, 4-(3-chloro-2-methylanilino)-3-thiophencarboxylic acid methyl ester (m. 80° to 82°) and 4-(2,6-difluoroanilino)-3-thiophencarboxylic acid methyl ester (m. 90° to 92°) are obtained analogously as products from 4-oxotetrahydro-3-thiophencarboxylic acid methyl ester and 2,6-dichloro-3-methylaniline, 3-chloro-2-methylaniline and 2,6-difluoroaniline, respectively.

4-(2-Chloroanilino)-5-methyl-3-thiophencarboxylic acid methyl ester (m. 64° to 65°) and 4-(2,6-dichloroanilino)-5-methyl-3-thiophencarboxylic acid methyl ester (m. 86°) are likewise obtained from 5-methyl-4-oxotetrahydro-3-thiophencarboxylic acid methyl ester and 2-chloroaniline and 2,6-dichloroaniline, respectively.

Alternatively, 3-(2,6-dichloroanilino)-4-methyl-2-thiophencarboxylic acid methyl ester (m. 110° to 112°) is obtained from 4-methyl-3-oxotetrahydro-2-thiophencarboxylic acid methyl ester and 2,6-dichloroaniline.

The procedure for the preparation of the anilinothiophencarboxylic acids is, alternatively, as follows:

15.9 g (0.1 mole) of 3-oxotetrahydro-2-thiophencarboxylic acid methyl ester, 14.2 g of 2-chloro-3-methylaniline and 200 mg of p-toluenesulfonic acid are heated in 500 ml of toluene for six hours using a water separator. 24.6 g (0.1 mole) of chloranil are then added, and the mixture is boiled for a further one hour. It is cooled and filtered; the filtrate is washed with 100 ml each of 2 N sodium hydroxide solution, sodium dithionite solution and water and concentrated; the residue is purified by column chromatography (silica gel, toluene/ethyl acetate 4/1). 3-(2-Chloro-3-methylanilino)-2-thiophencarboxylic acid methyl ester is obtained as an oil.

The following compounds: 3-(2,6-dichloroanilino)-2-thiophencarboxylic acid methyl ester, 3-(2,4-dichloro-5-methylanilino)-2-thiophencarboxylic acid methyl ester and 3-(2-chloro-5-methylanilino)-2-thiophencarboxylic acid methyl ester are obtained analogously from 3-oxotetrahydro-2-thiophencarboxylic acid methyl ester and 2,6-dichloroaniline, 2,4-dichloro-5-methylaniline and 2-chloro-5-methylaniline, respectively.

The saponification of the anilinothiophencarboxylic acid esters is carried out as follows:

3.16 g (0.1 mole) of 3-(2,6-dichloroanilino)-4-methyl-2-thiophencarboxylic acid methyl ester are boiled in 300 ml of methanol and 100 ml of 6 N potassium hydroxide solution for six hours. Methanol is then distilled off, and the mixture is taken up in water and washed with toluene. The aqueous phase is acidified and extracted with ether. The organic phase is dried, clarified with bleaching earth (for example Tonsil ®) and concentrated. Recrystallization of the residue from toluene gives 3-(2,6-dichloroanilino)-4-methyl-2-thiophencarboxylic acid (m. 157° to 158°).

4-(2-Chloroanilino)-3-thiophencarboxylic acid, 4-(2,6-dimethylanilino)-3-thiophencarboxylic acid, 4-(2-chloro-6-methylanilino)-3-thiophencarboxylic acid, 4-(4-methoxy-2-methylanilino)-3-thiophencarboxylic acid, 4-(2-chloro-3-methylanilino)-3-thiophencarboxylic acid and 4-(3-trifluoromethylanilino)-3-thiophencarboxylic acid are obtained analogously from 4-(2-chloroanilino)-3-thiophencarboxylic acid methyl ester, 4-(2,6-dimethylanilino)-3-thiophencarboxylic acid methyl ester, 4-(2-chloro-6-methylanilino)-3-thiophencarboxylic acid methyl ester, 4-(4-methyoxy-2-methylanilino)-3-thiophencarboxylic acid methyl ester, 4-(2-chloro-3-methylanilino)-3-thiophencarboxylic acid methyl ester and 4-(3-trifluoromethylanilino)-3-thiophencarboxylic acid methyl ester, respectively, by saponification.

(e) The oxotetrahydrothiophencarboxylic acids are known or are prepared as follows:

100 g (1 mole) of methacrylic acid methyl ester are added dropwise to 106 g of thioglycolic acid methyl ester and 1 ml of piperidine. The reaction mixture is added dropwise to a solution of 40 g of sodium methylate in 200 ml of methanol. The mixture is stirred for a further half an hour, poured onto water, acidified and extracted with methylene chloride and the organic phase is washed with water and dried with sodium sulfate. After distillation, 4-methyl-3-oxotetrahydro-2-thiophencarboxylic acid methyl ester is obtained (bp. 110° to 115°/14 Pascal).

5-Methyl-4-oxotetrahydro-3-thiophencarboxylic acid methyl ester (bp. 112°/14 Pascal) is obtained analogously from acrylic acid methyl ester and thiolactic acid methyl ester.

EXAMPLE 5

0.32 g (1 mmole) of 3-(2-chloro-6-methylanilino)-2-thiophenglyoxylic acid ethyl ester and 1 g of sodium boranate are warmed to 80° in 10 ml of dimethylformamide for 2 hours. The mixture is then poured onto water and washed with diethyl ether, and the aqueous phase is acidified and extracted with ethyl acetate. Concentration of the organic phase and column chromatography (silica gel/methylene chloride) give, in the first fraction, 3-(2-chloro-6-methylanilino)-2-thiophenacetic acid ethyl ester.

3-(2,6-Dichloroanilino)-2-thiophenacetic acid ethyl ester is obtained analogously from 3-(2,6-dichloroanilino)-2-thiophenglyoxylic acid ethyl ester by reduction with sodium boranate.

EXAMPLE 6

3.16 g (10 mmoles) of 3-(2,6-dichloroanilino)-2-thiophenglyoxylic acid and 2 g of sodium boranate are warmed to 80° in 10 ml of dimethylformamide for 4 hours. The mixture is poured onto water and extracted with toluene, the aqueous phase is acidified and extracted with ethyl acetate, and the organic phase is dried and concentrated. Recrystallization of the residue from toluene yields 3-(2,6-dichloroanilino)-2-thiophenacetic acid (m. 164° to 168°).

3-(2-Chloro-6-methylanilino)-2-thiophenacetic acid (m. 147° to 149°) and 3-(2,6-dichloroanilino)-4-methyl-2-thiophenacetic acid (m. 126° to 128°) are obtained analogously from 3-(2-chloro-6-methylanilino)-2-thiophenglyoxylic acid and 3-(2,6-dichloroanilino)-4-methyl-2-thiophenglyoxylic acid by reduction with sodium boranate and appropriate working up.

The starting compounds are obtained in the following manner:

(a) 3.44 g (10 mmoles) of 3-(2,6-dichloroanilino)-2-thiophenglyoxylic acid ethyl ester are dissolved in 10 ml of ethanol with 1 g of potassium hydroxide until a homogeneous solution has formed—after 10 minutes. The solution is diluted with 50 ml of water, acidified and extracted with ethyl acetate; the organic phase is dried and concentrated. Recrystallization from cyclohexane with a little toluene yields 3-(2,6-dichloroanilino)-2-thiophenglyoxylic acid.

3-(2-Chloro-6-methylanilino)-2-thiophenglyoxylic acid (m. 127° to 136°) and 3-(2,6-dichloroanilino)-4-methyl-2-thiophenglyoxylic acid (m. 126° to 128°) are obtained analogously from 3-(2-chloro-6-methylanilino)-2-thiophenglyoxylic acid ethyl ester and 3-(2,6-dichloroanilino)-4-methyl-2-thiophenglyoxylic acid ethyl ester by saponification with ethanolic potassium hydroxide solution.

(b) 2.44 g (10 mmoles) of 3-(2,6-dichloroanilino)thiophen, 1.01 g of triethylamine and 1.37 g (10 mmoles) of chlorooxalic acid ethyl ester are stirred in 20 ml of tetrahydrofuran at room temperature for 10 hours. 100 ml each of water and ethyl acetate are added, and the organic phase is dried and concentrated. Recrystallization of the residue from ethanol gives 3-(2,6-dichloroanilino)-2-thiophenglyoxylic acid ethyl ester.

3-(2-Chloro-6-methylanilino)-2-thiophenglyoxylic acid ethyl ester (m. 155° to 156°) and 3-(2,6-dichloroanilino)-4-methyl-2-thiophenglyoxylic acid ethyl ester are obtained analogously from 3-(2-chloro-6-methylanilino)thiophen and 3-(2,6-dichloroanilino)-4-methylthiophen and chlorooxalic acid ethyl ester.

(c) 2.88 g (10 mmoles) of 4-(2,6-dichloroanilino)-3-thiophencarboxylic acid (see Example 4d) are decarboxylated at 16 Pascal and 150° in a bulb tube distillation apparatus. Pure 3-(2,6-dichloroanilino)thiophen is obtained as the distillate.

3-(2-Chloro-6-methylanilino)thiophen and 3-(2,6-dichloroanilino)-4-methylthiophen are obtained analogously from 4-(2-chloro-6-methylanilino)-3-thiophencarboxylic acid and 3-(2,6-dichloroanilino)-4-methyl-2-thiophencarboxylic acid, respectively.

EXAMPLE 7

316.2 mg (1 mmole) of 4-(2,6-dichloroanilino)-3-thiophenacetic acid methyl ester are boiled in a solution of 11 ml of 2 N sodium hydroxide solution in 4.5 ml of water and 3 ml of methanol for one hour. The mixture is then diluted with 20 ml of water and extracted with 20 ml of methylene chloride; the aqueous phase is acidified.

The precipitate which has formed is filtered off and washed with 5 ml of diisopropyl ether. 4-(2,6-

Dichloroanilino)-3-thiophenacetic acid (m. 179° to 180°) is obtained.

5-Chloro-4-(2-chloro-6-methylanilino)-3-thiophenacetic acid (m. 143° to 146°) is obtained analogously from 5-chloro-4-(2-chloro-6-methylanilino)-3-thiophenacetic acid methyl ester by boiling with methanolic sodium hydroxide solution and appropriately working up the mixture.

EXAMPLE 8

330 mg (1 mmole) of 3-(2,6-dichloroanilino)-2-thiophenacetic acid ethyl ester are boiled with 1 g of potassium hydroxide in 5 ml of ethanol for one hour. The mixture is then diluted with 20 ml of water and extracted with 20 ml of methylene chloride. The aqueous solution is acidified, and the precipitate which has formed is filtered off and washed with 3 ml of diisopropyl ether. 3-(2,6-Dichloroanilino)-2-thiophenacetic acid (m. 164° to 168°) is obtained.

3-(2-Chloro-6-methylanilino)-2-thiophenacetic acid (m. 147° to 149°), 3-(2,6-dichloroanilino)-2-thiophenacetic acid (m. 164° to 168°) and 5-chloro-4-(2-chloro-6-methylanilino)-3-thiophenacetic acid (m. 143° to 146°) are obtained analogously from 3-(2-chloro-6-methylanilino)-2-thiophenacetic acid ethyl ester, 3-(2,6-dichloroanilino)-2-thiophenacetic acid methyl ester and 5-chloro-4-(2-chloro-6-methylanilino)-3-thiophenacetic acid methyl ester, respectively, by boiling with ethanolic potassium hydroxide solution and appropriately working up the mixture.

EXAMPLE 9

357 mg (1 mmole) of 4-(2,6-dichloroanilino)-3-thiophenacetic acid tert.-butyl ester are heated to the boil with 10 mg of p-toluenesulfonic acid in toluene for 2 hours. The reaction solution is washed with water, dried and concentrated to give 4-(2,6-dichloroanilino)-3-thiophenacetic acid (m. 179° to 180°).

The starting compound is obtained in the following manner:

316 mg (1 mmole) of 4-(2,6-dichloroanilino)-3-thiophenacetic acid methyl ester are warmed to 60° in 20 ml of tert.-butanol and 2 ml of concentrated sulfuric acid for 2 hours. The excess alcohol is distilled off. Chromatography on a column (silica gel/methylene chloride) gives, in the first fraction, 4-(2,6-dichloroanilino)-3-thiophenacetic acid tert.-butyl ester.

EXAMPLE 10

393 mg (1 mmole) of 4-(2,6-dichloroanilino)-3-thiophenacetic acid benzyl ester are subjected to hydrogenolysis (in a mixture of 100 ml of ethyl acetate and 10 ml of glacial acetic acid in a circulatory hydrogenation apparatus in the presence of 50 mg of 10 percent strength palladium-on-active charcoal at room temperature and under atmospheric pressure) until the theoretical amount of hydrogen has been taken up. The catalyst is filtered off, the filtrate is concentrated in vacuo, and the residue is dissolved in 1 N sodium hydroxide solution. The aqueous solution is extracted with toluene, and the product phase is acidified with 1 N hydrochloric acid and extracted again with toluene. The organic phase is dried and concentrated. 4-(2,6-Dichloroanilino)-3-thiophenacetic acid (m. 179° to 180°) is obtained.

The starting compound is obtained in the following manner:

316 mg (1 mmole) of 4-(2,6-dichloroanilino)-3-thiophenacetic acid methyl ester are introduced into a solution of 10 mg of potassium benzyl alcoholate in 20 ml of benzyl alcohol. The mixture is stirred at room temperature for 2 hours, excess alcohol is distilled off in vacuo and 4-(2,6-dichloroanilino)-3-thiophenacetic acid benzyl ester is obtained as the residue.

EXAMPLE 11

30.1 g (0.1 mole) of 4-(2,6-dichloroanilino)-3-thiophenacetamide are warmed to 100° in 135 ml of concentrated sulfuric acid and 49 ml of water for 3 hours. The mixture is poured onto ice, and the precipitate of 4-(2,6-dichloroanilino)-3-thiophenacetic acid which has formed is filtered off. The precipitate is boiled up with diisopropyl ether and dried; it then melts at 179° to 180°.

The starting compound is obtained in the following manner:

28.3 g (0.1 mole) of 4-(2,6-dichloroanilino)-3-thiophenacetonitrile are introduced into 150 ml of concentrated sulfuric acid and stirred for one hour at room temperature. It is poured onto ice, and the precipitate which has formed is filtered off. Recrystallization from ethyl acetate yields 4-(2,6-dichloroanilino)-3-thiophenacetamide (m. 172° to 173°).

EXAMPLE 12

A solution of 135 mg of sulfuryl chloride in 5 ml of methylene chloride is added dropwise to a solution of 283 mg (1 mmole) of 4-(2,6-dichloroanilino)-3-thiophenacetonitrile in 20 ml of methylene chloride at −15°. After 10 minutes, a sodium dithionite solution and 3 ml of 2 N sodium hydroxide solution are added. The organic phase is separated off, dried, clarified with bleaching earth (for example Tonsil ®) and concentrated. Recrystallization of the residue from methanol yields 5-chloro-4-(2,6-dichloroanilino)-3-thiophenacetonitrile (m. 128° to 128.5°).

5-Chloro-4-(2-chloro-6-methylanilino)-3-thiophenacetic acid methyl ester is obtained analogously from 4-(2-chloro-6-methylanilino)-3-thiophenacetic acid methyl ester by chlorination with sulfuryl chloride.

EXAMPLE 13

1.35 g (10 mmoles) of sulfuryl chloride in 20 ml of methylene chloride are added dropwise to a solution of 3.02 g (10 mmoles) of 4-(2,6-dichloroanilino)-3-thiophenacetic acid in 15 ml of methylene chloride at −15°. After 10 minutes, 10 ml each of 2 N NaOH and 10 percent strength (aq) sodium dithionite solution are added. The aqueous phase is separated off, acidified and extracted with ethyl acetate, and the product phase is dried and concentrated. Recrystallization of the residue from cyclohexane yields pure 5-chloro-4-(2,6-dichloroanilino)-3-thiophenacetic acid (d. 141° to 142°).

5-Chloro-4-(2-chloro-6-methylanilino)-3-thiophenacetic acid is obtained analogously from 4-(2-chloro-6-methylanilino)-3-thiophenacetic acid by chlorination with sulfuryl chloride.

EXAMPLE 14

2.84 g (10 mmoles) of N-(2,6-dichlorophenyl)-2,3-dihydro-2-oxothieno[3,4-b]pyrrole are boiled in 40 ml of methanol and 10 ml of 6 N KOH for half an hour. The mixture is diluted with 200 ml of water and extracted with toluene; the aqueous phase is acidified, and the precipitate of 4-(2,6-dichloroanilino)-3-thiophenacetic acid (which has formed) is filtered off. The precipitate is boiled up with diisopropyl ether and dried; it then melts at 179° to 181°.

The starting compound is obtained in the following manner:

1 g (0.33 mmole) of 4-(2,6-dichloroanilino)-3-thiophenacetic acid and 0.7 g (0.33 mmole) of phosphorus pentachloride are stirred in 10 ml of toluene at room temperature for half an hour. The mixture is extracted with water and sodium bicarbonate solution, clarified with bleaching earth (for example Tonsil ®) and concentrated. Recrystallization of the residue from isopropanol yields N-(2,6-dichlorophenyl)-2,3-dihydro-2-oxothieno[3,4-b]pyrrole (m. 187° to 188°).

EXAMPLE 15

2.83 g of 4-(2,6-dichloroanilino)-3-thiophenacetonitrile are introduced into 40 ml of diethylene glycol, which has been saturated with hydrochloric acid gas at 0°. The mixture is stirred at room temperature for one hour and poured onto water, the aqueous phase is extracted with ethyl acetate, and the product phase is washed several times with water, dried and concentrated. Recrystallization of the residue from cyclohexane yields pure 4-(2,6-dichloroanilino)-3-thiophenacetic acid 2-(2-hydroxyethoxy)ethyl ester (m. 58°).

EXAMPLE 16

5.28 g (17.5 mmoles) of 4-(2,6-dichloroanilino)-3-thiophenacetic acid are dissolved in 30 ml of chloroform together with 2.6 g (17.5 mmoles) of triethanolamine, and the solution is extracted by shaking with 20 ml of water. After evaporating off the water, the residue is taken up in ethanol and is crystallized in a crystallizing dish by evaporation. Triethanolammonium 4-(2,6-dichloroanilino)-3-thiophenacetate is obtained.

Piperazinium bis-[4-(2,6-dichloroanilino)-3-thiophenacetate] is obtained analogously.

EXAMPLE 17

30.2 g (0.1 mole) of 4-(2,6-dichloroanilino)-3-thiophenacetic acid are dissolved in 100 ml of a 1 N sodium hydroxide solution under the influence of heat. The solution is allowed to cool, and the sodium 4-(2,6-dichloroanilino)-3-thiophenacetate (which has precipitated) is filtered off (m. 247° to 250°).

Sodium 3-(2,6-dichloroanilino)-2-thiophenacetate (m. 229° to 232°) is analogously obtained.

EXAMPLE 18

10,000 tablets with an active compound content of 30 mg are prepared as described below:

300 g of 4-(2,6-dichloroanilino)-3-thiophenacetic acid, 800 g of maize starch, 550 g of lactose, 30 g of amorphous silicic acid and 40 g of sodium lauryl-sulfate are mixed, and the mixture is sieved. This mixture is moistened with a solution of 50 g of polyvinylpyrrolidone in 320 ml of ethanol and granulated through a sieve with a mesh width of 1.25 mm. The granules are dried at 40° and mixed with 160 g of pectin, 50 g of talc and 20 g of magnesium stearate. This mixture is pressed to tablets having a diameter of 8 mm and weighing 200 mg.

EXAMPLE 19

10,000 capsules with an active compound content of 25 mg are prepared as described below:

250 g of 4-(2,6-dichloroanilino)-3-thiophenacetic acid, 745 g of microcrystalline cellulose and 5 g of unpressed amorphous silicic acid are mixed thoroughly and filled into size 4 hard gelatin capsules.

EXAMPLE 20

Preparation of a batch of 1,000 suppositories.

2.450 kg of suppository base [Suppocire ® BM] are heated to 40° to 45°. 0.050 kg of 4-(2,6-dichloroanilino)-3-thiophenacetic acid (in the form of the sodium salt) is stirred into the melt.

The suppository mass is homogenized and then cast in molds.

EXAMPLE 21

Preparation of a batch of 100 liters of a suspension.

2.70 kg of Tylose ®C 30 are added to 90 l of water, while stirring vigorously; 1.00 kg of 4-(2,6-dichloroanilino)-3-thiophenacetic acid, 0.11 kg of sodium cyclamate and 0.08 kg of sorbic acid are then added. The mixture is made up to 100 liters (1) with water. It is passed through a corundum disc mill, subsequently degassed and then filled in 5 ml fractions.

EXAMPLE 22

Preparation of 100 liters of an injection solution.

65 l of distilled water are heated to 80°, while gassing with $N_2$; 2.000 kg of 4-(2,6-dichloroanilino)-3-thiophenacetic acid (in the form of the sodium salt) and 0.150 kg of prednisolone are then added. When everything has dissolved, the solution is cooled to room temperature, and 0.200 kg of sodium disulfite, 0.025 kg of cysteine hydrochloride and 26.00 kg of 1,2-propylene glycol are added; the mixture is then made up to 100 l with distilled water and stirred until a solution is formed.

PHARMACOLOGY

In addition to useful analgesic and antipyretic properties, the compounds of formula I and their salts have pronounced useful antiphlogistic properties, as is demonstrated, for example, by various tests in which the influence of the compounds on acute inflammatory reactions {carrageenin edema of the hind paw of rats [Winter et al.: Proc. Soc. exp. Biol. Med., 111 (1962) 544]}, on chronic inflammatory processes {Cotton pellet test on rats [Winter et al.: J. Pharmacol. exp. Therap., 141 (1963) 369]} and on adjuvant arthritis [based on the method of Perrine et al., Brit. J. Pharmacol., 21 (1963) 127] is determined. In these tests, the subject compounds are superior to prior-art compounds, for example previously-noted compounds of German Patent Specification No. 1,493,705 and commercially-available medicaments, such as indomethacin. Moreover, they are distinguished by their comparably-low toxicity.

The pronounced antiphlogistic, analgesic and antipyretic actions of the compounds according to the invention are demonstrated by comparison with the commercially-available compound 2 and with the compound 1 described in Arzneim.-Forsch. (Drug Res.), 20 (1970) 293 and 294. Table 1, which follows, identifies the compounds investigated by name and Serial No.

TABLE 1

| Serial No. | Name of Compound |
|---|---|
| 1 | 3-(2,6-dichloroanilino)thiophen-4-carboxylic acid |
| 2 | indomethacin |
| 3 | 4-(2,6-dichloroanilino)-3-thiophenacetic acid |
| 4 | 4-(2-chloro-6-methylanilino)-3-thiophenacetic acid |
| 5 | 4-(2,6-dichloro-3-methylanilino)-3-thiophenacetic acid |

TABLE 1-continued

| Serial No. | Name of Compound |
|---|---|
| 6 | 3-(2,6-dichloroanilino)-2-thiophenacetic acid |
| 7 | 4-(2-chloro-3-methylanilino)-3-thiophenacetic acid |
| 8 | 4-(3-chloro-2-methylanilino)-3-thiophenacetic acid |
| 9 | 4-(2,6-dimethylanilino)-3-thiophenacetic acid |
| 10 | 5-chloro-4-(2,6-dichloroanilino)-3-thiophenacetic acid |
| 11 | 3-(2-chloro-6-methylanilino)-2-thiophenacetic acid |
| 12 | 4-(2,6-difluoroanilino)-3-thiophenacetic acid |

Table 2 shows the acute antiphlogistic action, the toxicity and the therapeutic quotient of the compounds investigated.

TABLE 2

Antiphlogistic action of the compound according to the invention in an acute inflammation test - measured by the influence on carrageenin edema of the hind paw of rats - after single oral administration, and the lethal action in rats.

| Compound | Dose mg/kg, perorally | Maximum inhibition of carraggenin edema within 7 hours after oral administration of the substance % | $ED_{50}$* mg/kg perorally | Therapeutic quotient $LD_{50}/ED_{50}$ | Lethal action after administration for 7 days (rats) $LD_{50}$ mg/kg/day perorally |
|---|---|---|---|---|---|
| 1 | 10.0 | 31 | 56 | 2.1 | 120 |
|   | 100.0 | 57 | | | |
|   | 1.0 | 29 | | | |
| 2 | 3.0 | 47 | 4.6 | 1.2 | 5.5 |
|   | 10.0 | 56 | | | |
|   | 0.3 | 29 | | | |
| 3 | 1.0 | 46 | 1.6 | 6.9 | 11 |
|   | 3.0 | 56 | | | |
| 4 | 3.0 | 50 | 3 | >>6.7 | >>20 |
| 6 | 3.0 | 52 | ~3 | >>6.7 | >>20 |
| 8 | 3.0 | 49 | ~3 | >>10 | >>30 |
| 11 | 3.0 | 49 | ~3 | >>6.7 | >>20 |

*$ED_{50}$ = dose which causes a maximum edema inhibition of 50%.

The influence of the compounds to be tested on carrageenin edema of the hind paw of rats was determined as follows:

1 hour after oral administration of the compounds to be tested, female Sprague-Dawley rats (groups of 10 animals each; weight of each animal: 140 to 170 g), from which the feed (Altromin ®R, water ad libitum) had been withdrawn about 16 hours beforehand, are injected subplantarly in the right hind paw with 0.05 ml, per animal, of a 1 percent strength carrageenin suspension. The rats are kept at 24° C.

The paw volume of each rat is determined (2 to 3 individual measurements in each case) before edema provocation and at hourly intervals for 7 hours after edema provacation. The average percentage paw swelling of each treated group determined at the specified times after the carrageenin injection is related to that of the untreated control group (=100%).

The maximum percentage edema inhibition serves as a measure of the antiphlogistic action.

The paw volume is determined plethysmometrically. Measuring principle: the volume of liquid displaced through the paw of the rat is recorded digitally via an electromechanical pressure transducer (Statham P 23 V, 0–200 mm Hg).

The doses indicated for the compounds tested were administered in a volume of liquid of 20 ml/kg.

Table 3 and Table 4 show the chronic antiphlogistic action, the toxicity and the therapeutic quotient of the compounds investigated.

TABLE 3

Antiphlogistic action of the compound according to the invention in a chronic inflammation test - measured by the influence on the formation of granulation tissue after subcutaneous implantation of cotton (so-called cotton pellet test) - and the lethal action in rats after oral administration for 7 days

| Compound | Dose 7 x mg/ Kg/day orally | Inhibition of the formation of granulation tissue after treatment for 7 days % | $ED_{20}$* mg/kg/day perorally | Therapeutic quotient $LD_{50}/ED_{20}$ | Lethal action after oral administration for 7 days (rats) $LD_{50}$ mg/kg/day |
|---|---|---|---|---|---|
| | 0.1 | 7 | | | |
| | 0.3 | 11 | | | |
| | 1.0 | 16 | | | |
| 2 | 3.0 | 16 | ~3 | ~1.8 | 5.5 |
| | 4.0 | 17 | | | |
| | 5.0 | (25% dead) | | | |
| | 0.1 | 6 | | | |
| | 0.3 | 15 | | | |
| | 1.0 | 14 | | | |
| 3 | 3.0 | 22 | ~1 | ~11 | 11 |
| | 5.0 | 22 | | | |
| | 6.0 | 36 | | | |
| | | (0% dead) | | | |
| 5 | 1.0 | 16 | 1.6 | 5 | 8 |
| | 3.0 | 26 | | | |
| | 3.0 | 19 | | | |
| 7 | 10.0 | 27 | ~3.5 | >>5.7 | >>20 |
| 9 | 3.0 | 19 | ~3.0 | >>10 | >>30 |

*$ED_{20}$ = dose which causes an average inhibition of the formation of granulation tissue of 20%.

Experimental procedure for investigating the influence of the compounds to be tested on the formation of granulation tissue after implantation of cotton in rats (so-called cotton pellet method):

1 cotton pellet (manufacturer: Messrs. Hartmann/Heidenheim; cotton pellets size 2, No. 4865/2) which weighs 13.0±0.5 mg and has been impregnated beforehand with 0.1 ml of a solution of 0.5 mg of penicillin G and 0.8 mg of streptomycin sulfate/1 ml of distilled water is in each case implanted subcutaneously into the shoulder-blade region, on both sides, of male Sprague-Dawley rats (groups of 8 animals each; weight of each animal: 150 to 170 g) under diethyl ether anaesthesia and under sterile conditions. The cut skin is closed by means of clamps.

The compounds to be tested (in the form of the sodium salt in aqueous solution) or the corresponding amount (5 ml/kg/day) of tapwater (=control group) are administered orally each day on seven successive days. On the eighth day, the animals are killed and the cotton granules are exposed carefully, that is to say preserving the fibrous tissue capsule, dried (15 hours at 120°) and weighed. By substracting the weight of the cotton pellets, the amount of newly formed granulation tissue is obtained.

The percentage reduction in the average granuloma dry weight of a treated group compared with the control group (=100%) serves as a measure of the antiproliferative action of a compound.

TABLE 4

Antiarthritic action (so-called adjuvant arthritis; rats; $ED_{25}$; oral administration for 5 days) and toxicity ($LD_{50}$ in rats after oral administration for 7 days)

| Substance; Serial No. | Inhibition of adjuvant arthritis of 25% (= $ED_{25}$) in rats after oral administration for 5 days $ED_{25}$ mg/kg/day perorally | therapeutic quotient $LD_{50}/ED_{25}$ | $LD_{50}$ after administration for 7 days rats mg/kg/day orally |
|---|---|---|---|
| 1 | 9 | 13.3 | 120 |
| 2 | 0.18 | 30.6 | 5.5 |
| 3 | 0.20 | 55 | 11 |

The influence of the compounds to be tested on polyarthritis in rats caused by *Mycobacterium butyricum* (so-called "adjuvant arthritis") was determined using the experimental arrangement hereafter described: based on the method described by NEWBOULD and PERRINE et al. [NEWBOULD, B. B.; Brit. J. Pharmacol. 21, 127 (1963); and PERRINE, J. W. and TAKESUE, E. I.; Arch. int. Pharmacodyn., 174, 192 to 198 (1968)], so-called adjuvant arthritis, which manifests itself chiefly in a severe swelling of the tail (primary lesion) and of the paws (secondary lesion), is caused in rats by intradermal injection of a *Mycobact. butyricum* suspension in liquid paraffin into the base of the tail. Antiphlogistic agents inhibit this swelling reaction.

Tables 5 and 6 show the analgesic (inflammation pain) and antipyretic (yeast-induced fever) action of the compounds tested, in addition to the lethal action and therapeutic quotient.

TABLE 5

Analgesic action of the compound according to the invention after single oral administration - measured by the influence on the pain reaction (vocalization) provoked in rats by bending an inflamed ankle ($AgNO_3$ arthritis; inflammation pain) - and the toxicity in rats after administration for 7 days

| Compound | Dose mg/kg perorally | Analgesic action Inhibition of the pain reaction of % | $ED_{25}$* mg/kg perorally | $ED_{50}$* mg/kg perorally | Therapeutic quotients $LD_{50}/ED_{25}$ | Therapeutic quotients $LD_{50}/ED_{50}$ | Lethal action after oral administration for 7 days (rats) $LD_{50}$ mg/kg/day |
|---|---|---|---|---|---|---|---|
| 1 | 3 | 10 | | | | | |
| | 20 | 20 | | | | | |
| | | | 30 | 140 | 4 | 0.86 | 120 |
| | 100 | 40 | | | | | |
| | 200 | 60 | | | | | |
| 2 | 1 | 23 | | | | | |
| | 3 | 36 | 1.2 | 6 | 4.58 | 0.92 | 5.5 |
| | 6 | 50 | | | | | |
| 3 | 1 | 26 | | | | | |
| | 3 | 50 | 1 | 3 | 11 | 3.67 | 11 |
| | 10 | 62 | | | | | |

*$ED_{25}$ and $ED_{50}$ = dose which completely suppresses the pain reaction at the time of maximum action in 25 and 50% of the animals, respectively.

The influence of the compounds to be tested on the pain reaction provoked in rats by bending an inflamed tarsal joint ($AgNO_3$ inflammation) was determined as follows:

Based on the method of HOFFMEISTER et al. [*Arzneim. Forsch.*, 24, (1974) 600], 0.2 ml of a 1% strength silver nitrate solution is injected into the ankle joint (inside) of the right hind paw of female Sprague-Dawley rats (each animal weighing about 160 to 180 g) under ether anaesthesia. The animals are kept at 24° C. and are fed Altromin ®R and water ad libitum. After the $AgNO_3$ injection, almost all the animals (90 to 95%) can be made to cry out by moderate bending of the ankle joint. All the animals reacting positively are collected into groups of 10 animals. The compounds to be tested are administered orally in a volume of liquid of 10 ml/kg immediately after administration of the $AgNO_3$; the untreated control animals receive the corresponding amount of tapwater.

Over a period of 4 hours after administration of the substance, the number of animals reacting is determined at half hourly intervals.

The maximum percentage of the protected animals over a period of 4 hours after administration of the substance [relative to the number of animals in the control group reacting (=100%)] serves as a measure of the analgesic action.

TABLE 6

Antipyretic action of the compounds according to the invention
- measured by the influence of yeast-induced fever in rats
- after single oral administration, and the lethal action

| Compound | Dose mg/kg perorally | Maximum reduction in yeast-induced fever over a period of 7 hours after administration of the substance °C. | $ED_{1.5}$* mg/kg perorally | Therapeutic quotient $LD_{50}/ED_{2.5}$ | Lethal action after administration for 7 days (rats) $LD_{50}$ mg/kg/day |
|---|---|---|---|---|---|
| 1 | 1 | 0 | | | |
|   | 3 | 0.6 | | | |
|   | 10 | 1.7 | 8.2 | 14.6 | 120 |
|   | 30 | 2.1 | | | |
| 2 | 1 | 0.2 | | | |
|   | 3 | 0.7 | 5.0 | 1.1 | 5.5 |
|   | 6 | 1.8 | | | |
| 3 | 0.03 | 0.4 | | | |
|   | 0.1 | 0.8 | 0.4 | 27.5 | 11 |
|   | 0.3 | 1.4 | | | |
|   | 1.0 | 1.7 | | | |
| 4 | 0.3 | 1.4 | ~0.3 | >>66.7 | >>20 |
| 5 | 0.3 | 1.7 | <0.3 | >26.7 | 8 |
| 6 | 0.3 | 1.7 | <0.3 | >>66.7 | >>20 |
|   | 0.1 | 1.0 | | | |
| 9 | 0.3 | 1.5 | 0.3 | >100 | >30 |
|   | 1.0 | 2.3 | | | |
| 10 | 0.3 | 1.2 | 0.5 | >>40 | >>20 |
|   | 0.6 | 1.6 | | | |
| 12 | 0.3 | 0.5 | 0.9 | >33 | >30 |
|   | 1.0 | 1.6 | | | |

*$ED_{1.5}$ = dose which causes a maximum reduction in yeast-induced fever of 1.5° C.

The antipyretic action is determined by the influence of the compounds to be tested on yeast-induced fever in rats.

Hyperthermia is produced in female Sprague-Dawley rats (in groups of 5 animals; weight of each animal: 160 to 180 g) by subcutaneous injection (neck) of 10 ml/kg of a 20 percent strength aqueous brewer's yeast suspension (brewer's yeast "Heliosan"/Hefereformwerk Radolfzell). 24 hours after the yeast injection, the compounds to be tested are administered orally to the animals in a volume of liquid of 5 ml/kg, and a control group receives the corresponding amount of tapwater. The feed (Altromin ®R, water ad libitum) was withdrawn from the rats 18 hours beforehand. The rats are kept at about 23° C.

The body temperature is recorded 1 hour before administration of the substance and at hourly intervals after administration of the substance.

The maximum reduction in temperature (relative to the temperature before administration of the substance) in the course of 6 hours serves as a measure of the antipyretic action. The body temperature is measured with a temperature probe (Tastomed H, Braun electronic).

The superiority of the compounds according to the invention over those of the prior art is shown from the above data of Tables 2 to 6.

The invention and its advantages will be understood from the preceding description. Various changes may be made in the intermediates, in the synthesis, in the pharmacologically-active products, in the medicament compositions, in the dosage forms and in the method of use without departing from the spirit and scope of the invention or sacrificing its material advantages. The hereinbefore described intermediates, syntheses, pharmacologically-active compounds, medicament compositions, dosage forms and methods of use are merely illustrative of preferred embodiments of the invention.

What is claimed is:

1. A compound of the formula

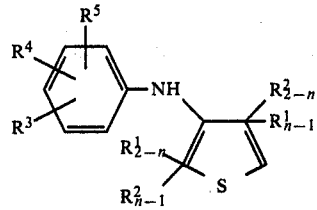

wherein
$R^1$ is a hydrogen atom (—H), chloro, bromo or methyl;
$R^2$ is —$CH_2$—COOH or —$CH_2$—$COOR^6$;
$R^3$ is —H, halo, lower alkyl, lower alkoxy or trifluoromethyl;
$R^4$ is one of the meanings of $R^3$;
$R^5$ is —H, halo or lower alkyl;
$R^6$ is benzyl, alkyl with from 1 to 5 carbon atoms or such alkyl which is substituted, any substituent of substituted alkyl being hydroxyl, hydroxy(lower-)alkoxy or lower alkanoyloxy; and
n is a positive whole number of at most 2;
or a salt of one of the acids.

2. A compound according to claim 1 wherein $R^2$ is —$CH_2$—COOH or a salt of such acid.

3. A compound according to claim 1 wherein $R^2$ is —$CH_2$—$COOR^6$.

4. A pharmacologically-acceptable compound according to claim 1.

5. A compound according to claim 1 wherein
$R^1$ is —H, chloro, bromo or methyl;
$R^2$ is —$CH_2$—COOH or —$CH_2$—$COOR^6$;
$R^3$ is —H, chloro, methyl, or trifluoromethyl;
$R^4$ is one of the meanings of $R^3$;
$R^5$ is —H or chloro;
$R^6$ is benzyl or alkyl having from 1 to 4 carbon atoms and optionally substituted by acetoxy or 2-hydroxyethoxy; and
n is 1
or a salt of one of the acids.

6. A compound according to claim 4 wherein
$R^1$ is —H or chloro;
$R^2$ is —$CH_2$—COOH or —$CH_2$—$COOR^6$;
$R^3$ is chloro, methyl or trifluoromethyl;
$R^4$ is chloro or methyl;
$R^5$ is —H or chloro;
$R^6$ is 2-(2-hydroxyethoxy)ethyl; and
n is 1;
or a salt of one of the acids.

7. A compound according to claim 4 wherein
$R^1$ is —H;
$R^2$ is —$CH_2$—COOH;
$R^3$ is chloro or methyl;
$R^4$ is chloro;
$R^5$ is —H; and
n is 1;
or a pharmacologically-tolerated salt thereof.

8. A compound according to claim 1 wherein
$R^1$ is —H or methyl;
$R^2$ is —$CH_2$—COOH or —$CH_2$—$COOR^6$;
$R^3$ is —H, chloro, methyl or trifluoromethyl;
$R^4$ is one of the meanings of $R^3$;

$R^5$ is —H or chloro;
$R^6$ is benzyl, $C_{1-4}$ alkyl, acetoxy-substituted $C_{1-4}$ alkyl or 2-hydroxyethoxy-substituted $C_{1-4}$ alkyl; and
n is 2;
or a salt of one of the acids.

9. A compound according to claim 4 wherein
$R^1$ is —H;
$R^2$ is —$CH_2$—COOH or —$CH_2$—$COOR^6$;
$R^3$ is chloro, methyl or trifluoromethyl;
$R^4$ is chloro or methyl;
$R^5$ is —H or chloro;
$R^6$ is 2-(2-hydroxyethoxy)ethyl; and
n is 2;
or a salt of one of the acids.

10. A compound according to claim 4 wherein
$R^1$ is —H,
$R^2$ is —$CH_2$—COOH;
$R^3$ is chloro or methyl,
$R^4$ is chloro,
$R^5$ is —H; and
n is 2;
or a pharmacologically-tolerated salt thereof.

11. A compound according to claim 7 wich is 4-(2,6-dichloroanilino)-3-thiophenacetic acid or a pharmacologically-tolerated salt thereof.

12. A medicament composition comprising at least one physiologically-active and pharmacologically-acceptable compound according to claim 1 which is an acid, a salt of such acid or an ester of such acid and at least one component which is substantially physiologically inert, the physiologically-active compound according to claim 1 comprising from 5 to 95 percent by weight of the composition.

13. A method of reducing pain, counteracting inflammation or lowering fever in a mammal so inflicted which comprises administering to the mammal an effective amount of a phrmacologically-active and physiologically-acceptable compound according to claim 1.

* * * * *